United States Patent [19]

Torii et al.

[11] Patent Number: 4,895,941
[45] Date of Patent: Jan. 23, 1990

[54] PROCESS FOR PREPARING 2α-METHYL-2β-(1,2,3-TRIAZOL-1-YL)METHYLPENAM-3α-CARBOXYLIC ACID DERIVATIVES

[75] Inventors: Sigeru Torii; Hideo Tanaka; Motoaki Tanaka, all of Okayama; Shozo Yamada, Honjyo; Akira Nakai, Okayama, all of Japan

[73] Assignees: Taiho Pharmaceutical Co., Ltd., Tokyo; Otsuka Kagaku Kabushiki Kaisha, Osaka, both of Japan

[21] Appl. No.: 316,631

[22] Filed: Feb. 28, 1989

[30] Foreign Application Priority Data

Mar. 1, 1988 [JP] Japan .................. 63-49039

[51] Int. Cl.$^4$ .................. C07D 499/00; A61K 31/425
[52] U.S. Cl. .................................. 540/310
[58] Field of Search ............... 540/370; 514/192, 193

[56] References Cited

U.S. PATENT DOCUMENTS

| | | | |
|---|---|---|---|
| 4,496,484 | 1/1985 | Micetich et al. | 260/245.2 |
| 4,529,592 | 7/1985 | Micetich et al. | 424/114 |
| 4,562,073 | 12/1985 | Micetich et al. | 540/310 |
| 4,668,514 | 5/1987 | Micetich et al. | 540/310 |
| 4,774,238 | 9/1988 | Broom et al. | 540/310 |

OTHER PUBLICATIONS

Tetrahedron Letters No. 38, pp. 3303–3306 (1975).
Micetich et al., Synthesis 1986, 292 published Apr., 1986.

Primary Examiner—Nicholas S. Rizzo
Attorney, Agent, or Firm—Armstrong, Nikaido, Marmelstein, Kubovcik & Murray

[57] ABSTRACT

2α-Methyl-2β-(1,2,3-triazol-1-yl)methylpenam-3α-carboxylic acid derivatives are prepared by reacting a penicillanic acid sulfoxide derivative of the formula

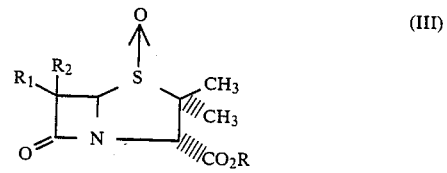

wherein R is a penicillin carboxyl protecting group, and $R_1$ is hydrogen or halogen, $R_2$ is hydrogen, lower alkyl or the like with a triazole derivative of the formula

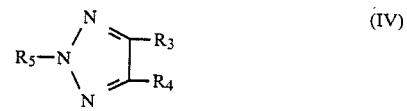

wherein $R_3$ and $R_4$ are hydrogen, trialkylsilyl, lower alkyl, lower alkoxy or the like and $R_5$ is hydrogen or silyl substituted with 3 groups selected from the class consisting of lower alkyl, benzyl and phenyl in a solvent.

12 Claims, No Drawings

PROCESS FOR PREPARING 2α-METHYL-2β-(1,2,3-TRIAZOL-1-YL)METHYLPENAM-3α-CARBOXYLIC ACID DERIVATIVES

The present invention relates to a novel process for preparing a 2α-methyl-2β-(1,2,3-triazol-1-yl)methylpenam-3α-carboxylic acid derivative, and more particularly to a process for preparing a 2α-methyl-2β-(1,2,3-triazol-1-yl)methylpenam-3α-carboxylic acid derivative by introducing a 1,2,3-triazolyl group into the 2β-methyl group.

The 2α-methyl-2β-(1,2,3-triazol-1-yl)methylpenam-3α-carboxylic acid derivative produced by the process of the invention is represented by the formula

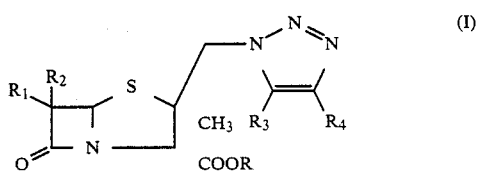

wherein R is a penicillin carboxyl protecting group, $R_1$ is hydrogen atom or halogen atom, $R_2$ is hydrogen atom, lower alkyl group, lower alkoxy group, halogen atom, azido group, lower alkylthio group, phthalimido group or $-NHR_6$ group (wherein $R_6$ is hydrogen atom or acyl group), $R_3$ and $R_4$ are the same or different and each represent hydrogen atom, trialkylsilyl group, lower alkyl group, lower alkoxy group, substituted or unsubstituted phenyl group, lower acyl group, trifluoromethyl group, carbamoyl group, lower alkyl-substituted carbamoyl group, lower alkoxy-substituted lower alkyl group, hydroxyl group, nitro group, amino group, cyano group, formyl group, halogen atom, a group of the formula $-S(O)_nR_7$ (wherein $R_7$ is lower alkyl, n is 0, 1 or 2), a group of the formula $-COOR_8$ (wherein $R_8$ is hydrogen atom, substituted or unsubstituted benzyl group, alkali metal atom, alkyl group having 1 to 18 carbon atoms, lower alkenyl or lower alkynyl group) or lower alkyl group substituted with 1 to 3 phenyl groups.

The compound of the formula (I) is useful as the intermediate for producing a 2α-methyl-2β-(1,2,3-triazol-1-yl)methylpenam-3β-carboxylic acid-1,1-dioxide derivative having a potent β-lactamase inhibitory activity and represented by the formula

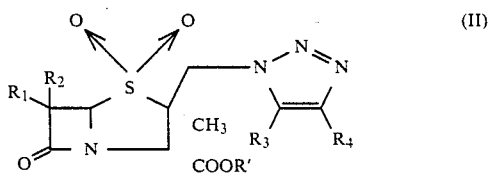

wherein $R_1$, $R_2$, $R_3$ $R_4$ are as defined above, R' is hydrogen atom or a penicillin carboxyl protecting group which can be readily metabolized or hydrolyzed in vivo to give a carboxyl group.

The compound of the formula (II) is disclosed in U.S. Pat. Nos. 4,529,592, 4,562,073 and 4,668,514 and J. Med. Chem. Vol. 30, 1469 (1987).

Known processes for preparing the compound of the formula (II) include, for example, those described, in U.S. Pat. Nos. 4,529,592, 4,562,073 and 4,668,514, Synthesis, 1986, 292 and J. Med. Chem. Vol. 30, 1469 (1987). The disclosed processes are conducted in the following manner.

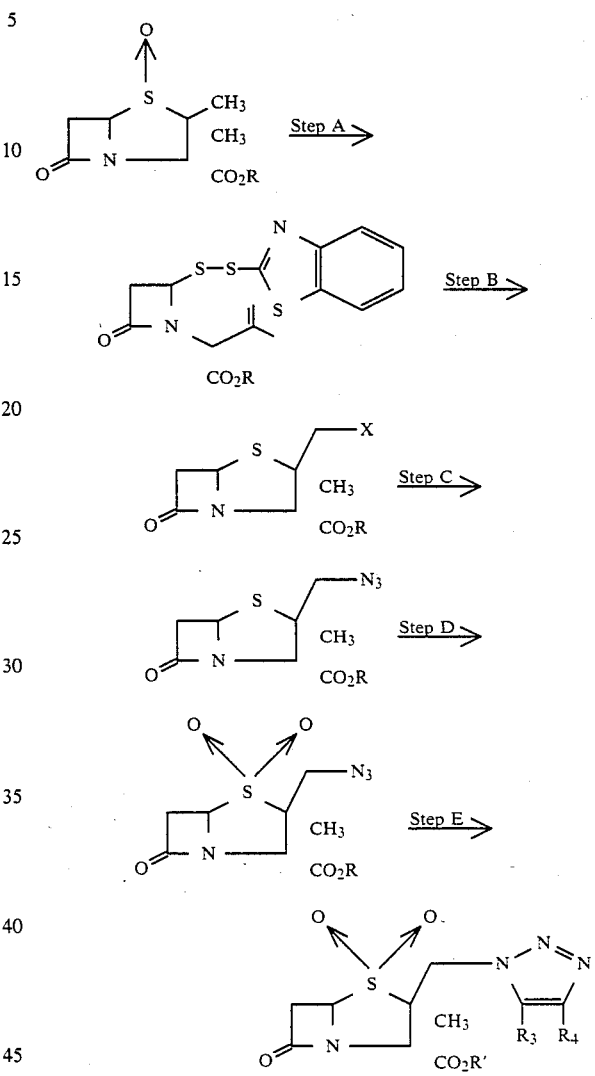

In the foregoing formulas, $R_3$, $R_4$, R and R' are as defined above and X is halogen atom.

In the foregoing reaction scheme, the penicillin acid sulfoxide derivative is converted to an azetidinone disulfide derivative in step A, which is then converted to a 2β-halogenomethyl penicillin derivative in step B. The 2β-halogenomethyl penicillin derivative is converted to an azide compound in step C. The azide compound is then oxidized in step D and the resulting sulfone is reacted with an acetylene derivative in step E to give a compound of the formula (II).

However, said process for preparing the compound of the formula (II) poses various problems as described below. First, the process necessitates a number of reaction steps and entails difficulty in selectively introducing the triazole ring into a specific position so that the desired compound is produced in significantly low yields of about 9 to about 27%. Further, the process invariably forms as an intermediate the 2β-halogenomethyl penicillin derivative which is unstable and hence cumbersome to handle. Additionally the process requires the use of acetylene compound and azide compound which threaten the danger of explosion and which therefore should be handled in small amounts with due safety measure. Thus the above prior art process is not commercially advantageous.

We conducted extensive research on the reaction between a penicillanic acid sulfoxide derivative and a triazole derivative and found a novel process for preparing a 2α-methyl-2β-(1,2,3-triazol-1-yl)methylpenam-3α-carboxylic acid derivative, the process being undisclosed in literature and being capable of producing the derivative in a good yield with a simple procedure and capable of introducing a triazolyl group region-selectively. The present invention has been accomplished on the basis of this novel finding.

The present invention provides a 2α-methyl-2β-(1,2,3-triazol-1-yl)methylpenam-3β-carboxylic acid derivative represented by the formula

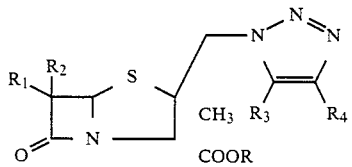

wherein R is a penicillin carboxyl protecting group, $R_1$ is hydrogen atom or halogen atom, $R_2$ is hydrogen atom, lower alkyl group, lower alkoxy group, halogen atom, azido group, lower alkylthio group, phthalimido group or —$NHR_6$ group (wherein $R_6$ is hydrogen atom or acyl group), $R_3$ and $R_4$ are the same or different and each represent hydrogen atom, trialkylsilyl group, lower alkyl group, lower alkoxy group, substituted or unsubstituted phenyl group, lower acyl group, trifluoromethyl group, carbamoyl group, lower alkyl-substituted carbamoyl group, lower alkoxy-substituted lower alkyl group, hydroxyl group, nitro group, amino group, cyano group, formyl group, halogen atom, a group of the formula —$S(O)_nR_7$ (wherein $R_7$ is lower alkyl, n is 0, 1 or 2), a group of the formula —$COOR_8$ (wherein $R_8$ is hydrogen atom, substituted or unsubstituted benzyl group, alkali metal atom, alkyl group having 1 to carbon atoms, lower alkenyl or lower alkynyl group) or lower alkyl group substituted with 1 to 3 phenyl groups, the process comprising reacting a penicillanic acid sulfoxide derivative represented by the formula

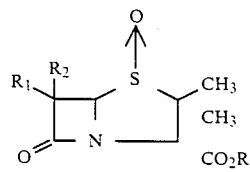

wherein R, $R_1$ and $R_2$ are as defined above, with a triazole derivative represented by the formula

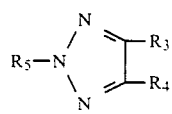

wherein $R_3$ and $R_4$ are as defined above and $R_5$ is hydrogen atom or silyl group substituted with 3 groups selected from the class consisting of lower alkyl group, benzyl group and phenyl group.

The process of the invention requires only one step to produce the compound of the formula (I), which in turn can be easily oxidized, thereby producing the above β-lactamase inhibitory compound of the formula (II) in a good yield. The process of the invention can be conducted with simple procedure without requiring the use of dangerous reactants, and hence is commercially advantageous.

Throughout the specification and claims, the term "lower" used in conjunction with "alkyl" or "alkoxy" is intended to indicate that each alkyl or alkoxy portion therein can contain 1 to 6 carbon atoms, particularly 1 to 4 carbon atoms.

Penicillin carboxyl protecting groups represented by R include known carboxyl protecting groups which are conventionally used in the synthesis of penicillins, and examples thereof are described in Japanese Unexamined Patent Publication No. 49-81380 and in "Cephalosporins and Penicillins, Chemistry and Biology" edited by H. E. Flynn published in 1972 by Academic Press. Preferable examples of the group R are methyl, ethyl, propyl, butyl, tert-butyl, 1,1-dimethylpropyl, 1-cyclopropylmethyl, 2-cyano-1,1-dimethylethyl, p-bromobenzoylmethyl, p-nitrobenzoylmethyl, dimethylaminomethyl, methylthiomethyl, phenylthiomethyl, succinimidomethyl, trichloroethyl, tribromoethyl, 1,1-dimethyl-2-propenyl, 1,3-dimethyl-3-butenyl, benzyl, diphenylmethyl, trityl, p-nitrobenzyl, p-methoxybenzyl, di(p-methoxyphenyl)methyl, acetoxymethyl, acetoxyethyl, propionyloxyethyl, pivaloyloxymethyl, pivaloyloxyethyl, pivaloyloxypropyl, benzoyloxymethyl, benzoyloxyethyl, benzylcarbonyloxymethyl, cyclohexylcarbonyloxymethyl, methoxymethyl, ethoxymethyl, benzyloxymethyl, 3-phthalidyl, crotonolacton-4-yl, tetrahydropyranyl, dimethylaminoethyl, dimethylchlorosilyl, trichlorosilyl, pyridine-1-oxide-2-methyl, quinoline-1-oxide-2-methyl and the like.

Examples of the halogen atoms represented by $R_1$ or $R_2$ are chlorine, bromine and the like. Examples of the lower alkyl group and the lower alkyl group of the lower alkylthio group represented by $R_2$ are straight-chain or branched-chain alkyl groups having 1 to 6 carbon atoms such as methyl, ethyl, propyl, isopropyl, butyl, isobutyl, tert-butyl, pentyl, hexyl and the like. Examples of the lower alkoxy group are straight- or branched-chain alkoxy groups having 1 to 6 carbon atoms such as methoxy, ethoxy, propoxy, isopropoxy, butoxy, isobutoxy, tert-butoxy, pentoxy, hexyloxy and the like.

The acyl groups represented by $R_6$ are acyl groups derived from straight- or branched-chain or cyclic organic carboxylic acids which may contain unsaturated bond, nitrogen atom, oxygen atom, sulfur atom, etc. Examples of such acyl groups are conventional acyl groups constituting acylamino groups which are bonded to the 6-position of penicillin derivatives or to the 7-position of cephalosporin derivatives. Specifically, said organic carboxylic acids from which said acyl groups are derived are (a) an aromatic carboxylic acid wherein an aromatic hydrocarbon group is directly bonded to a carboxyl group, (b) a heterocyclic carboxylic acid wherein a heterocyclic group is directly bonded to a carboxyl group, (c) straight- or branched-chain or cyclic aliphatic carboxylic acid which may contain oxygen atom or sulfur atom in its saturated or unsaturated carbon chain and (d) an acid wherein an aromatic hydrocarbon group or heterocyclic group is bonded, either directly or via an oxygen or sulfur atom, to a straight- or branched-chain or cyclic aliphatic carboxylic acid which may contain oxygen atom or sulfur atom in its saturated or unsaturated carbon chain, such as, for example, aromatic hydrocarbon group-substituted aliphatic carboxylic acid, aromatic hydrocarbon group-thio-substituted aliphatic carboxylic acid, aromatic hydrocarbon group-oxy-substituted aliphatic carboxylic acid, heterocyclic group-substituted aliphatic carboxylic acid, heterocyclic group-oxy-substituted aliphatic carboxylic acid, heterocyclic group-thio-substituted aliphatic carboxylic acid, etc. Examples of said aliphatic carboxylic acids are $C_1$–$C_{10}$ straight- or branched-chain or $C_4$–$C_7$ cyclic aliphatic carboxylic acids, such as formic acid, acetic acid, propionic acid, butanoic acid, isobutanoic acid, pentanoic acid, isopentanoic acid, hexanoic acid, cyclopropanecarboxylic acid, cyclobutanecarboxylic acid, cyclopentanecarboxylic acid, cyclohexanecarboxylic acid, acrylic acid, crotonic acid, cyclohexylacetic acid, cyclohexenylacetic acid, methoxyacetic acid, ethoxyacetic acid, cyclohexyloxyacetic acid, methylthioacetic acid, etc. Examples of said aromatic hydrocarbon group in the organic carboxylic acids are phenyl, naphthyl and the like. Examples of said heterocyclic groups in the above organic carboxylic acids are residues formed by removing a hydrogen atom from saturated or unsaturated and monocyclic or polycyclic, particularly bicyclic, heterocyclic compounds which contain at least one hetero atom, particularly 1 to 4 hetero atoms, including nitrogen, oxygen or sulfur in the ring structure, such as thiophene, furan, pyridine, pyrimidine, pyrrole, pyrazole, imidazole, triazole, thiazole, isothiazole, oxazole, isoxazole, thiadiazole, oxadiazole, tetrazole, benzotriazole, benzimidazole, etc. The aliphatic carboxylic acid, aromatic hydrocarbon group and heterocyclic group constituting the above organic carboxylic acid may optionally have at least one, particularly 1 to 3, substituents which do not adversely affect the reaction. The substituents include, for example, halogen atom such as fluorine, chlorine, bromine or iodine, hydroxyl group, amino group, nitro group, cyano group, sulfonic acid group, carboxyl group, lower alkyl group, lower alkoxy group, lower alkoxyimino group, etc. Preferable examples of the acyl groups represented by $R_6$ are 2-thienylacetyl, phenylacetyl, phenoxyacetyl, furylacetyl, pyridylacetyl, pyrimidylacetyl, oxazolylacetyl, oxadiazolylacetyl, thiazolylacetyl, thiadiazolylacetyl, triazolylacetyl, tetrazolylacetyl, 2-aminothiazol-4-yl-acetyl, α-syn-methoxyimino-α-(2-aminothiazol-4-yl)acetyl, {D(-)-α-(4-ethyl-2,3-dioxo-1-piperazinecarboxamido)-α-4-hydroxyphenyl}acetyl, {(Z)-2-(2-aminothiazol-4-yl)-2-(2-carboxypropyloxyimino)}acetyl, formyl, acetyl, propionyl, tetrazolylthioacetyl, 4-pyridylthioacetyl, 4-pyridyloxyacetyl, benzoyl, p-nitrobenzoyl, 4-isoxazolylcarbonyl, etc.

It is preferable that $R_1$ is hydrogen atom or halogen atom and that $R_2$ is hydrogen atom, halogen atom, azido group, phthalimido group or group —$NHR_6$ wherein $R_6$ is as defined above.

Specific examples of the groups represented by $R_3$ and $R_4$ in the above formula (I) are as follows. Examples of trialkylsilyl groups are tri(lower alkyl)silyl groups such as trimethylsilyl, ethyldimethylsilyl, n-propyldimethylsilyl, tert-butyldimethylsilyl, triethylsilyl, triisopropylsilyl, etc. Examples of lower alkyl groups are straight- or branched-chain alkyl groups having 1 to 6 carbon atoms such as methyl, ethyl, propyl, isopropyl, butyl, isobutyl, sec-butyl, tert-butyl, pentyl, hexyl, etc. Examples of lower alkoxy groups are straight- or branched-chain alkoxy groups having 1 to 6 carbon atoms such as methoxy, ethoxy, propoxy, isopropoxy, butoxy, isobutoxy, tert-butoxy, pentoxy, hexyloxy, etc. The substituted phenyl groups may have 1 to 5 substituents, particularly 1 to 3 substituents, such a fluorine, chlorine, bromine, iodine and like halogen atom, lower alkyl group, lower alkoxy group, nitro group, etc. Examples of such substituted phenyl groups are tolyl, xylyl, 2-ethylphenyl, 4-ethylphenyl, 2,4,6-trimethylphenyl, 2-methoxyphenyl, 4-methoxyphenyl, 2,4-dimethoxyphenyl, 4-chlorophenyl, 4-bromophenyl, 2,4-dichlorphenyl, 4-fluorophenyl, 4-bromophenyl, etc. Examples of lower acyl groups are $C_2$–$C_6$ aliphatic acyl groups such as acetyl, propionyl, butyryl, valeyl, pivaloyl, etc. Examples of the halogen atoms are fluorine, chlorine, bromine, iodine, etc. Examples of lower alkoxy-substituted lower alkyl groups are methoxymethyl, ethoxymethyl, propyloxymethyl, butoxymethyl, methoxyethyl, ethoxyethyl, propyloxyethyl, butoxyethyl, etc. Examples of the lower alkyl-substituted carbamoyl groups are methylcarbamoyl, ethylcarbamoyl, propylcarbamoyl, butylcarbamoyl, pentylcarbamoyl, isopropylcarbamoyl, tertbutylcarbamoyl, etc. Examples of the group represented by the formula —$S(O)_nR_7$ are —$SCH_3$, —$SC_2H_5$, —$SC_3H_7$, —$SO$—$CH_3$, —$SO$—$C_2H_5$, —$SO$—$C_3H_7$, —$SO_2$—$CH_3$, —$SO_2$—$C_2H_5$, —$SO_2$—$C_3H_7$, etc. The substituted benzyl groups represented by $R_8$ may have 1 to 5 substituents, particularly 1 to 3 substituents, such as fluorine, chlorine, bromine, iodine and like halogen atom, lower alkyl group, lower alkoxy group, nitro group, etc. Examples of such substituted benzyl groups are o-nitrobenzyl, p-nitrobenzyl, m-nitrobenzyl, p-chlorobenzyl, m-chlorobenzyl, o-fluorobenzyl, p-bromobenzyl, o-methylbenzyl, p-ethylbenzyl, m-propylbenzyl, 4-nitro-4-ethylbenzyl, 2,4-dinitrobenzyl, 2,4,6-trinitrobenzyl, 2,4-dimethylbenzyl, 2,4,6-triethylbenzyl, p-methoxybenzyl, o-methoxybenzyl, p-ethoxybenzyl, m-propoxybenzyl, 2,4-dimethoxybenzyl, etc. Examples of the alkali metal atoms are lithium, sodium, potassium, etc. Examples of $C_1$–$C_{18}$ alkyl groups include lower alkyl groups as defined above and $C_7$–$C_{18}$ alkyl groups such as heptyl, octyl, decyl, undecyl, tetradecyl, octadecyl, etc. Examples of lower alkenyl groups are $C_2$–$C_6$ alkenyl groups such as propenyl, butenyl, pentenyl, hexenyl, etc. The lower alkynyl groups are $C_2$–$C_6$ alkynyl groups such as propynyl, butynyl, pentynyl, hexynyl, etc. Examples of lower alkyl groups substituted with 1 to 3 phenyl groups are benzyl, phenylethyl, diphenylmethyl, trityl, etc.

It is preferable that $R_3$ and $R_4$ are the same or different and each represent hydrogen atom, tri(lower alkyl)silyl group, lower alkyl group, lower alkoxy group, substituted or unsubstituted phenyl group, lower acyl group, trifluoromethyl group, carbamoyl group or a group of the formula —$COOR_8$ wherein $R_8$ is as defined above.

Examples of the silyl groups represented by $R_5$ and substituted with 3 groups selected from the class consisting of lower alkyl, benzyl and phenyl are tri(lower alkyl)silyl groups as exemplified above, diphenylmethylsilyl, dimethylphenylsilyl, tert-butyldiphenylsilyl, triphenylsilyl, tribenzylsilyl, etc.

The compounds of the formula (III) are known compounds and can be prepared by known method, for example, by the methods described in J. Chem. Soc. Perkin trans. I, 1772-1775 (1976), Japanese Unexamined Patent Publications No. 53-137951 and No. 54-3094.

The process of the invention is usually conducted by reacting a penicillanic acid sulfoxide derivative of the formula (III) with a triazole derivative of the formula (IV) in a suitable solvent with heating. The triazole derivative of the formula (IV) is used in an amount of about 1 to about 10 moles, preferably about 2 to about 4 moles, per mole of the compound of the formula (III). The solvents to be used in the reaction are not particularly limited as far as they do not adversely affect the reaction, and include nitrile solvents such as acetonitrile, propionitrile and butyronitrile, halogenated hydrocarbon solvents such as 1,2-dichloroethane, 1,2-dichloropropane and 1,1,2-trichloroethane, ketone solvents such as methyl ethyl ketone and diethyl ketone, ether solvents such as dimethoxyethane and dioxane. When a solvent having a boiling point of below 110° C. is used, better results are usually obtained by conducting the reaction in a sealed tube with heating. The reaction temperature is about 90° to about 150° C., preferably about 110° to about 120° C. The reaction pressure is not critical in the invention and may range from about 1 to about 5 atms, preferably about 1 to about 3 atms. When the reaction is conducted in a sealed tube with heating, the reaction system is under the pressure of the vapor pressure of the solvent and reactants used. If desired, it is possible to add to the reaction system a dehydrating agent such as magnesium sulfate or an acid catalyst such as 2-pyridine-carboxylic acid, but such are not essential in the present invention. The reaction time is about 1 to about 8 hours, and generally the reaction is completed within about 3 to 5 hours.

After completion of the reaction, the desired product can be isolated and purified by a conventional method such as recrystallization, column chromatography or the like.

If desired, the substituents $R_1$ and $R_2$ at the 6-position of the compound of the formula (I) can be removed or converted to hydrogen atoms in high yields of at least 90% by a conventional method, for example, by the methods disclosed in J. Med. Chem., 24, 1531-1534 (1981), Japanese Unexamined Patent Publication No. 62-294686, etc.

The resulting compound of the formula (I), when subjected to conventional oxidation reaction, can readily give a 1,1-dioxide compound of the formula (II) having a β-lactamase activity. The oxidization reaction is carried out by a conventional method using a conventional oxidizing agent such as potassium permanganate, periodic acid, perbenzoic acid, m-chloroperbenzoic acid, hydrogen peroxide, etc. The oxidizing agent may be used in excess, but is preferably used in an amount of about 1 to about 5 moles per mole of the compound of the formula (I). Examples of the solvent can be any of those which does not affect the oxidation reaction and include dichloromethane, chloroform, carbon tetrachloride, pyridine, tetrahydrofuran, dioxane, acetone, formic acid, dimethylformamide, ethyl acetate, water and the like. The reaction temperature is not particularly limited but generally about 0° to about 60° C.

If desired, the compound of the formula (II) thus prepared may be subjected to a conventional reaction for changing the carboxyl protecting group to a carboxyl protecting group which can be readily metabolized in vivo or to a conventional de-esterification reaction for changing the carboxyl protecting group into a free acid form. Such reactions are described, for example, in "Design of prodrugs," pages 3-6, edited by Hans Bundgaard 1985, Elsevier Science Publishers B. V. (Biological Division).

Furthermore, the compound of the formula (I) prepared by the process of the present invention can be converted to compounds useful as antibiotics by changing the protecting group R by a conventional method into a group capable of forming an ester to be easily hydrolyzed in vivo, or by a conventional de-esterification of the protecting group R into a free acid form or by being made into a pharmaceutically acceptable salt by a conventional method. Such reactions are also described, for example, in "Design of prodrugs," pages 3-6, edited by Hans Bundgaard 1985, Elsevier Science Publishers B. V. (Biological Division).

The present invention will be described below in more detail with reference to the following examples.

EXAMPLE 1

Preparation of benzhydryl 2α-methyl-2β-(1,2,3-triazol-1-yl)methylpenam-3α-carboxylate A 2 g quantity of benzhydryl penicillanate 1-β-oxide, 1.8 ml of 2-trimethylsilyl-1,2,3-triazole and 20 ml of acetonitrile were mixed and heated at 115°-120° C. for 4 hours in a sealed tube. After cooling, acetonitrile was distilled off and the residue obtained was subjected to silica gel column chromatography (eluent: benzene-ethyl acetate=4:1). The resulting oily product was crystallized from methanol, giving 1.09 g of colorless benzhydryl 2α-methyl-2β-(1,2,3-triazol-1-yl)methylpenam-3α-carboxylate (yield: 48%).

Melting point: 141°-143° C.

Infrared absorption spectrum (KBr)
$\nu_{CO}$ (cm$^{-1}$) = 1760, 1740

Nuclear magnetic resonance spectrum (CDCl$_3$)
δ (ppm) = 1.22 (3H, s)
3.18, 3.67 (each 1H, ABX, $J_{AB}$=16 Hz, $J_{AX}$=4 Hz, $J_{BX}$=2 Hz);
4.59 (2H, s);
4.86 (1H, s);
5.39-5.45 (1H, m);
6.90 (1H, s);
7.33 (10H, s);
7.73 (2H, s).

EXAMPLE 2

Preparation of benzhydryl 2α-methyl-2β-(1,2,3-triazol-1-yl)methylpenam-3α-carboxylate A 2 g quantity of benzhydryl penicillanate 1-β-oxide, 1.8 ml of 2-trimethylsilyl-1,2,3-triazole and 20 ml of acetonitrile were mixed and heated at 115°-120° C. for 4 hours in a sealed tube in the presence of 1 g of dried magnesium sulfate. After cooling, magnesium sulfate was filtered off and the filtrate was concentrated. The residue was treated in the same manner as in Example 1, giving 1.18 g of benzhydryl 2-α-methyl-2β-(1,2,3-triazol-1yl)methylpenam-3α-carboxylate (yield: 52%).

The melting point, infrared absorption spectrum (KBr) and nuclear magnetic resonance spectrum (CDCl$_3$) were identical with those of the product of Example 1.

EXAMPLE 3

Preparation of benzhydryl 2α-methyl-2β-(1,2,3-triazol-1-yl)methylpenam-3α-carboxylate A 2 g quantity of benzhydryl penicillanate 1-α-oxide, 1.8 ml of 2-trimethylsilyl-1,2,3-triazole and 20 ml of acetonitrile were mixed and heated at 115°–120° C. for 4 hours in a sealed tube. After cooling, the mixture obtained was treated in the same manner as in Example 1 to prepare 1.11 g of benzhydryl 2α-methyl-2β-(1,2,3-triazol-1-yl)methylpenam-3α-carboxylate (yield: 49%).

The melting point, infrared absorption spectrum (KBr) and nuclear magnetic resonance spectrum (CDCl$_3$) were identical with those of the product of Example 1.

EXAMPLE 4

Preparation of benzhydryl 2α-methyl-2β-(1,2,3-triazol-1-yl)methylpenam-3α-carboxylate A 200 mg quantity of benzhydryl penicillanate 1-β-oxide, 210 mg of 2-t-butyldimethylsilyl-1,2,3-triazole and 2 ml of acetonitrile were mixed and heated at 118°–120° C. for 4 hours in a sealed tube. After cooling, the resulting mixture was treated in the same manner as in Example 1 to produce 115 mg of benzhydryl 2α-methyl-2β-(1,2,3-triazol-1-yl)methylpenam-3α-carboxylate (yield: 51%).

The melting point, infrared absorption spectrum (KBr) and nuclear magnetic resonance spectrum (CDCl$_3$) were identical with those of the product of Example 1.

EXAMPLE 5

Preparation of p-methoxybenzyl 2α-methyl-2β-(1,2,3-triazol-1-yl)methylpenam-3α-carboxylate A 337 mg quantity of p-methoxybenzyl penicillanate 1-α-oxide, 0.4 ml of 2-trimethylsilyl-1,2,3-triazole and 3 ml of acetonitrile were mixed and heated at 120°–122° C. for 4 hours in a sealed tube. After cooling, the reaction mixture was subjected to silica gel column chromatography (eluent: benzene-ethyl acetate=5:1), giving 175 mg of p-methoxybenzyl 2α-methyl-2β-(1,2,3-triazol-1-yl)methylpenam-3α-carboxylate as an oily product (yield: 45%).

Infrared absorption spectrum (neat)
$\nu_{CO}$ (cm$^{-1}$) = 1775, 1735
Nuclear magnetic resonance spectrum (CDCl$_3$)
δ (ppm) = 1.34 (3H, s)
3.03, 3.53 (each 1H, ABX, $J_{AB}$=16 Hz, $J_{AX}$=4 Hz, $J_{BX}$=2 Hz);
3.80 (3H, s);
4.58 (2H, s);
4.74 (1H, s);
5.10 (2H, s);
5.36–5.42 (1H, m);
6.83 (2H, d, J=8 Hz);
7.26 (2H, d, J=8 Hz);
7.68–7.77 (2H, m).

EXAMPLE 6

Preparation of p-methoxybenzyl 2β-(4,5-dimethoxycarbonyl-1,2,3-triazol-1-yl)methyl-2α-methylpenam-3β-carboxylate A 337 mg quantity of p-methoxybenzyl penicillanate 1-α-oxide, 555 mg of 4,5-dimethoxycarbonyl-1,2,3-triazole and 13 mg of 2-pyridinecarboxylic acid were mixed in 4 ml of methyl ethyl ketone and heated at 130° C. for 4.5 hours with stirring. After cooling, the reaction mixture was subjected to silica gel column chromatography (eluent: benzene-ethyl acetate =6:1), thereby giving 207 mg of p-methoxybenzyl 2β-(4,5-dimethoxycarbonyl-1,2,3-triazol-1-yl)methyl-2α-methylpenam-3α-carboxylate as an oily product (yield 41%).

Infrared absorption spectrum (neat)
$\nu_{CO}$ (cm$^{-1}$) = 1770, 1735, 1720
Nuclear magnetic resonance spectrum (CDCl$_3$)
δ (ppm) = 1.33 (3H, s); 3.16, 3.54 (each 1H, ABX, $J_{AB}$=16 Hz, $J_{AX}$=4 Hz, $J_{BX}$=2 Hz);
3.80 (3H, s);
3.97 (6H, s);
4.92 (2H, s);
4.98 (1H, s);
5.12 (2H, s);
5.33 (1H, dd, J=2, 4 Hz);
6.92 (2H, d, J=8 Hz);
7.28 (2H, d, J=8 Hz).

EXAMPLE 7

Preparation of p-methoxybenzyl 2s-(4,5-dimethoxycarbonyl-1,2,3-triazol-1-yl)methyl-2α-methylpenam-3α-carboxylate A 337 mg quantity of p-methoxybenzyl penicillanate 1-α-oxide, 566 mg of 4,5-dimethoxycarbonyl-2-trimethylsilyl-1,2,3-triazole and 2 ml of acetonitrile were mixed and heated at 120°–122° C. for 4 hours in a sealed tube. After cooling, the reaction mixture was treated in the same manner as in Example 6 to produce 232 mg of p-methoxybenzyl 2β-(4,5-dimethoxycarbonyl-1,2,3-triazol-1-yl)methyl-2α-methylpenam-3α-carboxylate (yield: 46%).

The infrared absorption spectrum (neat) and nuclear magnetic resonance spectrum (CDCl$_3$) were identical with those of the product of Example 6.

EXAMPLE 8

Preparation of benzhydryl 6α-bromo-2α-methyl-2β-(1,2,3-triazol-1-yl)methylpenam-3α-carboxylate A 120 mg quantity of benzhydryl 6α-bromopenicillanate 1-β-oxide, 154 mg of 2-trimethylsilyl-1,2,3-triazole and 1 ml of acetonitrile were mixed and heated at 110° C. for 4 hours in a sealed tube. The reaction mixture was diluted with dichloromethane and washed with water and the organic layer was washed with an aqueous solution of sodium bicarbonate. The organic layer separated was dried over magnesium sulfate and the solvent was distilled off under reduced pressure. The residue was subjected to silica gel column chromatography (eluent: benzene-ethyl acetate=3:1) to produce 49 mg of benzhydryl 6α-bromo-2α-methyl-2β-(1,2,3-triazol-1-yl)methylpenam-3α-carboxylate (yield: 37%).

Infrared absorption spectrum (KBr)
$\nu_{CO}$ (cm$^{-1}$) = 1780, 1745
Nuclear magnetic resonance spectrum (CDCl$_3$)

δ(ppm)=1.20 (3H, s);
4.50 (2H, s);
4.92 (1H, d, J=1.5 Hz);
5.02 (1H, s);
5.47 (1H, d, J=1.5 Hz);
6.87 (1H, s);
7.28 (10H, m);
7.57 (2H, s).

EXAMPLE 9

Preparation of benzhydryl 6,6-dibromo-2α-methyl-2β-(1,2,3-triazol-1-yl)methylpenam-3α-carboxylate A 141 mg quantity of benzhydryl 6,6-dibromopenicillanate 1-α-oxide, 149 mg of 2-trimethylsilyl-1,2,3-triazole and 1 ml of acetonitrile were mixed and heated at 110° C. for 4 hours in a sealed tube. The reaction mixture was diluted with dichloromethane and washed with water and the organic layer was washed with an aqueous solution of sodium bicarbonate. The organic layer separated was dried over magnesium sulfate and the solvent was distilled off under reduced pressure. The residue was subjected to silica gel column chromatography (eluent: benzene-ethyl acetate=6:1), thereby giving 35 mg of benzhydryl 6,6-dibromo-2α-methyl-2β-(1,2,3-triazol-1-yl)methylpenam-3α-carboxylate (yield: 23%).

Infrared absorption spectrum (KBr)
$\nu_{CO}$ (cm$^{-1}$)=1785, 1745
Nuclear magnetic resonance spectrum (CDCl$_3$)
δ (ppm)=1.17 (3H, s);
4.41, 4.65 (each 1H, AB, J=14 Hz);
5.00 (1H, s);
5.88 (1H, s);
6.87 (1H, s);
7.17 (10H, m);
7.68 (1H, d, J=1.5 Hz);
7.80 (1H, d, J=1.5 Hz).

EXAMPLE 10 Preparation of trichloroethyl 2α-methyl-6β-phenylacetylamino-2β-(1,2,3-triazol-1-yl)methylpenam-3α-carboxylate A 154 mg quantity of trichloroethyl 6β-phenylacetylamino-penicillanate 1-β-oxide, 149 mg of 2-trimethylsilyl-1,2,3-triazole and 1 ml of acetonitrile were mixed and heated at 110° C. for 4 hours in a sealed tube. After cooling, the reaction mixture was treated in the same manner as in Example 8 to prepare 45 mg of trichloroethyl 2α-methyl-6β-phenylacetylamino-2β-(1,2,3-triazol-1-yl)methylpenam-3α-carboxylate (yield: 34%).

EXAMPLE 11

Preparation of p-nitrobenzyl 2α-methyl-6β-phenoxyacetylamino-2β-(1,2,3-triazol-1-yl)methylpenam-3α-carboxylate A 138 mg quantity of p-nitrobenzyl 6β-phenoxyacetylamino-penicillanate 1-β-oxide, 150 mg of 2-trimethylsilyl-1,2,3-triazole and 1 ml of acetonitrile were mixed and heated at 110° C. for 4 hours in a sealed tube. After cooling, the reaction mixture was treated in the same manner as in Example 8, giving 36 mg of p-nitrobenzyl 2α-methyl-6β-phenoxyacetylamino-2β-(1,2,3-triazol-1-yl)methylpenam-3α-carboxylate (yield: 30%).

REFERENCE EXAMPLE 1

Preparation of benzhydryl 2α-methyl-2β-(1,2,3-triazol-1-yl)methylpenam-3α-carboxylate 1,1-dioxide A 913 mg quantity of benzhydryl 2α-methyl-2β-(1,2,3-triazol-1-yl)methylpenam-3α-carboxylate was dissolved in a mixture of 5.4 ml of acetone and 1.8 ml of water and then 2.5 ml of acetic acid was added thereto. Thereafter to the resulting mixture was added 664 mg of potassium permanganate with ice-cooling and stirring, followed by stirring at room temperature for 3 hours. To the reaction mixture obtained was added 30% aqueous solution of hydrogen peroxide until the reaction mixture became colorless and the precipitate was collected by filtration. The precipitate thus obtained was recrystallized from methanol to give 882 mg of the title compound (yield: 90%).

Melting point: 206–208° C. (decomposition)
Infrared absorption spectrum (KBr)
$\nu_{CO}$ (cm$^{-1}$)=1800, 1760
Nuclear magnetic resonance spectrum (DMSO-d$_6$)
δ (ppm)=1.13 (3H, s)
3.34, 3.77 (each 1H, ABX, $J_{AB}$=16.48 Hz, $J_{AX}$=4.40 Hz, $J_{BX}$=0.22 Hz);
4.96, 5.30 (each 1H, AB, $J_{AB}$=15.60 Hz);
5.26 (3H, s);
7.00 (1H, s);
7.34–7.48 (10H, m);
7.77 (1H, d, J=0.88 Hz);
7.96 (1H, d, J=0.88 Hz).

We claim:

1. A process for preparing a 2α-methyl-2β-(1,2,3-triazol-1-yl)methylpenam-3α-carboxylic acid derivative represented by the formula

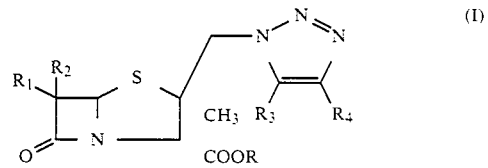

wherein R is a penicillin carboxyl protecting group, $R_1$ is hydrogen atom or halogen atom, $R_2$ is hydrogen atom, lower alkyl group, lower alkoxy group, halogen atom, azido group, lower alkylthio group, phthalimido group or —NHR$_6$ group, wherein R$_6$ is hydrogen atom or acyl group derived from a carboxylic acid, $R_3$ and $R_4$ are the same or different and each represent hydrogen atom, trialkylsilyl group, lower alkyl group, lower alkoxy group, phenyl group, phenyl group which has 1 to 5 substituents selected from the group consisting of halogen atom, lower alkyl group, lower alkoxy group and nitro group, C$_2$–C$_6$ aliphatic acyl group, trifluoromethyl group, carbamoyl group, lower alkyl-substituted carbamoyl group, lower alkoxy-substituted lower alkyl group, hydroxyl group, nitro group, amino group, cyano group, formyl group, halogen atom, a group of the formula —S(O)$_n$R$_7$, wherein R$_7$ is lower alkyl, n is 0, 1 or 2, a group of the formula —COOR$_8$, wherein R$_8$ is hydrogen atom, benzyl group, benzyl group which has 1 to 5 substituents selected from the group consisting of halogen atom, lower alkyl group, lower alkoxy group and nitro group, alkali metal atom, alkyl group having 1 to 18 carbon atoms, lower alkenyl or lower alkynyl group, or lower alkyl group substituted with 1 to 3 phenyl groups, which comprises heating a penicillanic acid sulfoxide derivative represented by the formula

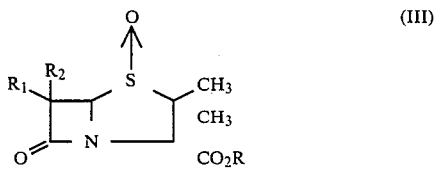

wherein R, $R_1$ and $R_2$ are as defined above, with about 1-10 moles of a triazole derivative represented by the formula

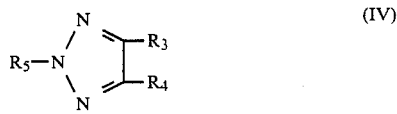

wherein $R_3$ and $R_4$ are as defined above and $R_5$ is hydrogen atom or silyl group substituted with 3 groups selected from the group consisting of lower alkyl group, benzyl group and phenyl group.

2. A process as defined in claim 1 wherein $R_1$ is halogen atom or halogen atom and $R_2$ is hydrogen atom, halogen atom, azido group, phthalimido group or a group —$NHR_6$ wherein $R_6$ is as defined in claim 1.

3. A process as defined in claim 1 wherein $R_1$ is hydrogen atom or halogen atom and $R_2$ is hydrogen atom, halogen atom or a group —$NHR_6$ wherein $R_6$ is phenylacetyl or phenoxyacetyl.

4. A process as defined in claim 1 wherein $R_3$ and $R_4$ are the same or different and each represent hydrogen atom, tri(lower alkyl)silyl group, lower alkyl group, lower alkoxy group, substituted or unsubstituted phenyl group, $C_2$–$C_6$ aliphatic acy group, trifluoromethyl group, carbamoyl group or a group of the formula —$COOR_8$ wherein $R_8$ is as defined in claim 1.

5. A process as defined in claim 1 wherein $R_3$ and $R_4$ each represent hydrogen atom or a group of the formula —$COOR_8$ wherein $R_8$ is $C_1$–$C_{18}$ alkyl group.

6. A process as defined in claim 1 wherein the triazole derivative of the formula (IV) is used in an amount of about 2 to about 4 moles per mole of the penicillanic acid sulfoxide derivative of the formula (III).

7. A process as defined in claim 1 wherein the reaction is conducted in a solvent with heating at about 90° to about 150° C.

8. A process as defined in claim 1 wherein the reaction is conducted in a solvent having a boiling point of below 110° C. in a sealed tube with heating at about 90° to about 150° C.

9. A process as defined in claim 1 wherein the reaction is conducted in a solvent having a boiling point of below 110° C. in a sealed tube with heating at about 110° to about 120° C.

10. A process as defined in claim 1 wherein the solvent is nitrile, halogenated hydrocarbon, ketone or ether.

11. A process as defined in claim 1 wherein the solvent is acetonitrile, propionitrile, butyronitrile, 1,2-dichloroethane, 1,2-dichloropropane, 1,1,2-trichloroethane, methyl ethyl ketone, diethyl ketone, dimethoxyethane or dioxane.

12. A process as defined in claim 1, wherein $R_6$ is 2-thienylacetyl, phenylacetyl, phenoxyacetyl, furylacetyl, pyridylacetyl, pyrimidylacetyl, oxazolylacetyl, oxadiazolylacetyl, thiazolylacetyl, thiadiazolylacetyl, triazolylacetyl, tetrazolylacetyl, 2-aminothiazol-4-ylacetyl, α-syn-methoxyiminoα-(2-aminothiazol-4-yl)acetyl, {D(—)-α-(4-ethyl-2,3-dioxo-1-piperazinecarboxamido)-α-4-4hydroxyphenyl}-acetyl, {(Z)-2-(2-aminothiazol-4-yl)-2-(2-carboxypropyloxyimino)}-acetyl, formyl, acetyl, propionyl, tetrazolylthioacetyl, 4-pyridylthioacetyl, 4-pyridyloxyacetyl, benzoyl, p-nitrobenzoyl or 4-isoxazolylcarbonyl.

* * * * *

UNITED STATES PATENT AND TRADEMARK OFFICE
CERTIFICATE OF CORRECTION

PATENT NO. : 4,895,941
DATED : January 23, 1990
INVENTOR(S) : Sigeru TORII et al It is certified that error appears in the above-identified patent and that said Letters Patent is hereby corrected as shown below:

Column 1, Line 18, Formula (I), change " 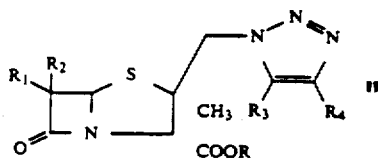 "

to -- 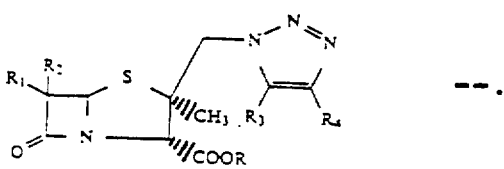 --.

Column 1, Line 52, Formula (II), change " 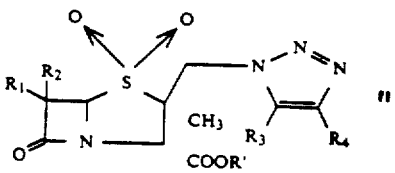 "

to -- 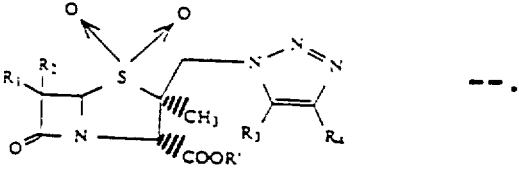 --.

UNITED STATES PATENT AND TRADEMARK OFFICE
CERTIFICATE OF CORRECTION

PATENT NO.  : 4,895,941
DATED       : January 23, 1990
INVENTOR(S) : Sigeru TORII et al It is certified that error appears in the above-identified patent and that said Letters Patent is hereby corrected as shown below:

Column 2, Line 5, in the Formula,
change:                                           to:

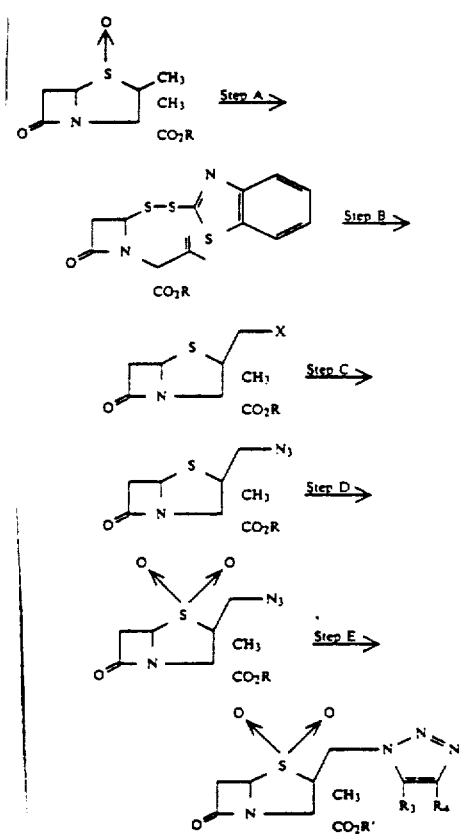
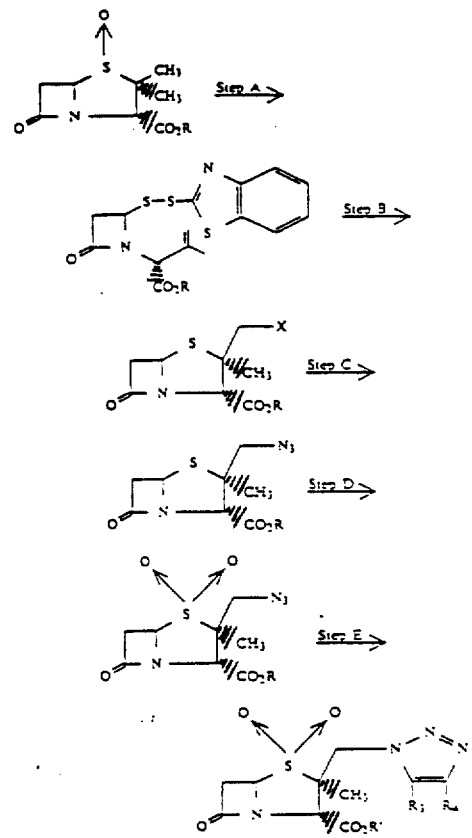

UNITED STATES PATENT AND TRADEMARK OFFICE
CERTIFICATE OF CORRECTION

PATENT NO. : 4,895,941

DATED : January 23, 1990

INVENTOR(S) : Sigeru TORII et al

It is certified that error appears in the above-identified patent and that said Letters Patent is hereby corrected as shown below:

Column 3, Line 51, Formula (III), change " 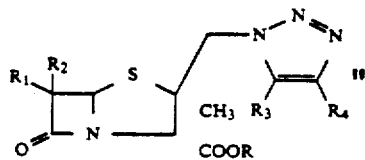 "

to -- 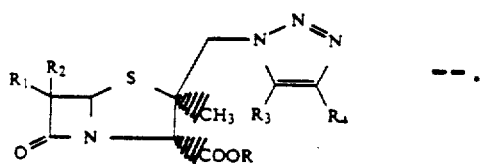 --.

Column 3, Line 20, Formula (I), change " 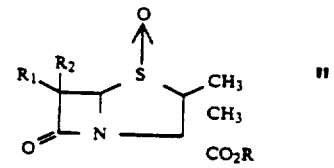 "

to -- 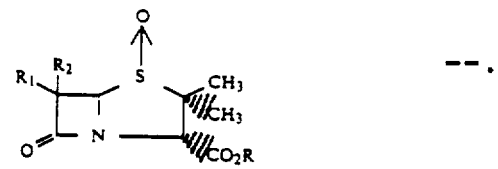 --.

Column 10, Example 7, line 32, change "2s" to -- 2β --.

UNITED STATES PATENT AND TRADEMARK OFFICE
CERTIFICATE OF CORRECTION

PATENT NO. : 4,895,941

DATED : January 23, 1990

INVENTOR(S) : Sigeru TORII et al

It is certified that error appears in the above-identified patent and that said Letters Patent is hereby corrected as shown below:

Column 12:

Claim 1, Line 38, Formula (I), change "  "

to -- 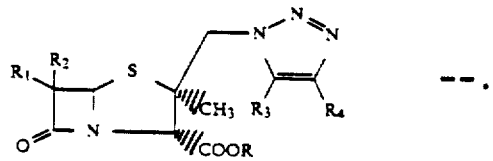 --.

Column 13:

Claim 1, Line 6, Formula (III), change " 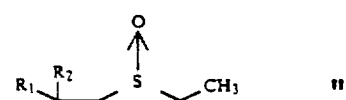 "

to -- 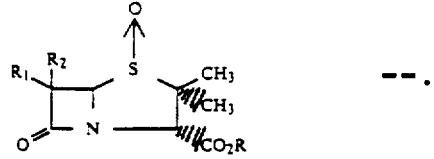 --.

UNITED STATES PATENT AND TRADEMARK OFFICE
CERTIFICATE OF CORRECTION

PATENT NO. : 4,895,941

DATED : January 23, 1990

INVENTOR(S) : Sigeru Torii, et al

It is certified that error appears in the above-indentified patent and that said Letters Patent is hereby corrected as shown below:

Column 13, Claim 4, line 41, change "acy" to -- acyl --.

Column 14, Claim 12, line 34, change "methoxyiminoα" to -- methoxyimino-α --.

Column 14, Claim 12, line 36, change "4hydroxyphenyl)-acetyl" to -- hydroxyphenyl)acetyl --.

Column 14, Claim 12, line 37, change "-acetyl" to -- acetyl --.

Signed and Sealed this

Twenty-fourth Day of May, 1994

Attest:

BRUCE LEHMAN

*Attesting Officer*         *Commissioner of Patents and Trademarks*